United States Patent [19]

Davis

[11] Patent Number: 4,963,264

[45] Date of Patent: Oct. 16, 1990

[54] PROCESS FOR SELECTIVE DIALYSIS USING POLYMERIC AFFINITY ADSORBENTS AND SIZE SELECTIVE MEMBRANES

[75] Inventor: James C. Davis, Hudson, Ohio

[73] Assignee: The Standard Oil Company, Cleveland, Ohio

[21] Appl. No.: 742,872

[22] Filed: Jun. 10, 1985

[51] Int. Cl.⁵ .............................................. B01D 61/26
[52] U.S. Cl. ..................................... 210/638; 210/648
[58] Field of Search .................... 210/638, 927, 500.2, 210/259, 651, 648

[56] References Cited

U.S. PATENT DOCUMENTS

| | | | |
|---|---|---|---|
| 3,519,558 | 7/1986 | Cooper et al. | 210/23 |
| 3,808,267 | 4/1974 | Davis et al. | 260/527 R |
| 3,957,504 | 5/1976 | Ho et al. | 210/638 X |
| 4,163,714 | 8/1979 | Gregor | 210/23 F |
| 4,247,393 | 1/1981 | Wallace | 210/927 X |
| 4,375,414 | 3/1983 | Strahilevitz | 210/638 |
| 4,474,690 | 10/1984 | Nylen | 260/112 R |
| 4,515,906 | 5/1985 | Friesen et al. | 521/28 |
| 4,523,998 | 6/1985 | Kim | 210/638 |
| 4,563,337 | 1/1986 | Kim | 423/24 |
| 4,741,831 | 5/1988 | Grinstead | 210/638 |

FOREIGN PATENT DOCUMENTS 2458066  6/1975  Fed. Rep. of Germany ...... 210/638

OTHER PUBLICATIONS

"Copper Selective Ion-Exchange Resin with Improved Iron Rejection" R. R. Grinstead, *Journal of Metals,* vol. 31, No. 3 (1979) 13–16.

"Membrane-Based Solvent Extraction for Selective Removal and Recovery of Metals" B. M. Kim, *Journal of Membrane Science,* 21 (1984) 5–19.

Primary Examiner—Frank Spear
Attorney, Agent, or Firm—Larry W. Evans; Joseph G. Curatolo; Sue E. Phillips

[57] ABSTRACT

A process for the selective dialysis of liquid streams containing different materials comprises the steps of providing a porous membrane in a cell, the membrane having pores of sufficient dimension to allow passage of the different materials therethrough, circulating an affinity adsorbent stream against a first side of the membrane, where the adsorbent has a dimension larger than that of the pores and has a binding capacity for at least one but not all of the different materials and, passing the liquid stream containing the different materials against a second side of the membrane whereby certain of the materials become bound to the adsorbent upon passing through the membrane to the first side thereof and become separated from others of the materials which can return to the second side of the membrane. A separate stripping process is also provided which can be employed in conjunction with the dialysis process or alone where it is desirable to remove bound materials from an affinity adsorbent material.

18 Claims, 3 Drawing Sheets

PROCESS FOR SELECTIVE DIALYSIS USING POLYMERIC AFFINITY ADSORBENTS AND SIZE SELECTIVE MEMBRANES

TECHNICAL FIELD

The subject invention is directed toward a unique process which employs dialysis for the selective removal of ionic and organic species or particles from solutions, streams and the like. Generally, any flow stream which contains a desirable material or a contaminant material, for which a known adsorbent exists, can be treated with this process for separation and removal of specific materials.

Such a process can be used for water softening in the same manner as ion exchange resins are without the associated difficulties of manufacturing a high quality resin bead and attaching the appropriate active ion exchange group. Other applications for this process include the selective removal of anions such as amino acids and carboxylates as well as chromates and gold cyanide complexes from plating solutions and desirable cations such as, but not limited to, copper, silver, nickel, cobalt, chromium, vanadium, platinum, lead, tin, zirconium, and rare earth metals from streams such as plating wastes, photographic processes, and liquors from mining operations. Still another application would include continuous ion exchange chromatography.

Organic applications include the use of monoclonal antibodies or other biological materials selectively to purify streams containing desirable hormones or other pharmaceuticals such as optical isomers. In addition, this process can be useful in purifying process streams such as contaminated organic materials like gasoline or other fuels by removing salts and water through the use of appropriate adsorbents known to the art. Another use would be the separation of similar organic species such as glucose/fructose mixtures.

BACKGROUND ART

The known art for the selective extraction of desired materials from feed streams falls into three general categories. First among these is resin bead extraction typified by ion exchange resins which have been used selectively to extract species such as transition metal ions from aqueous solutions. Specific chelating resins with selectivity for one or more desirable metal ions are also known but are difficult to manufacture, consequently expensive, and suffer from severe bead attrition due to physical breaking up of the beads in flow systems. The difficulty of attaching desirable chelating groups to available macroporous resin beads limits the quantity and selectivity of the materials which can be made using this technique.

One relatively recent publication "Copper-Selective Ion-Exchange Resin with Improved Iron Rejection" R. R. Grinstead, *Journal of Metals,* Vol. 31, No. 3 (1979) 13–16, describes a then improved chelating resin for copper/iron ion solutions, highly selective for copper.

The present invention overcomes the disadvantages above by using affinity adsorbents such as chelating polymers, ground ion exchange resins and enzymes all of variable and wide ranges of molecular weight or particle size, thus providing easier synthesis as well as eliminating the bead attrition problem. Additionally, the advantage of continuous operation can be easily realized with the present invention without the problems associated with fluidized bed systems for continuous ion exchange.

A second process involves solvent extraction which is typically used to recover mineral values using selective extractants soluble in solvents, immiscible with the feed solvent. Large volumes of solvent and extractant inventory are required, however, and valuable extractant is commonly lost due to solubility in the feed stream and entrainment losses resulting from microfine solvent/extractant particles which do not coalesce in the solvent/feed separators.

More recently, patent and open literature references have suggested the use of membranes as separators to avoid the solvent/extractant losses due to entrainment.

U.S. Pat. No. 3,808,267 teaches a membrane process for recovery of $C_2$ to $C_4$ carboxylic acids from dilute aqueous solution with one side of a microporous membrane while the other side is contacted with a liquid organic solvent for the acid.

"Membrane-Based Solvent Extraction for Selective Removal and Recovery of Metals", B. M. Kim, *Journal of Membrane Science,* 21 (1984) 5–19, describes a process for stripping industrial metals from wastewater. The process employs two modules, one for extraction through which the aqueous waste water stream flows, routed through thousands of very thin hollow fibers. An organic solvent containing a liquid ion-exchange material flows between the fibers and collects metal ions migrating through the pores in the fibers. The organic solvent stream then flows through a stripping module wherein an acid, base or salt solution, as appropriate, removes the metal ions.

In both cases these references discuss the use of immiscible solvents as the means of separating the extractant from the feed stream since the extractants used are small enough to permeate through the membranes employed. Both solvent and extractant soluble losses do occur in these systems and result in organic pollution of the feed stream. Inasmuch as the membranes in the present invention can be selected and operated in a manner which will prevent loss of the polymeric adsorbent as will be detailed hereinbelow, such organic pollution is eliminated. It is believed that an improvement in permeation rate may also be realized due to the lack of a solvent/feed interfacial barrier in the subject process.

Membrane methods comprise the third category for the selective removal of materials from solutions. In most instances these methods have been pressure driven ultrafiltration or reverse osmosis processes as opposed to the concentration gradient driven process of the present invention. U.S. Pat. No. 4,163,714 describes the preparation of pressure driven affinity sorption membranes from a membrane filter which is composed of an insoluble matrix polymer or interpolymer complex. The membranes are employed by passing material-containing solutions therethrough where one or more of the materials forms a complex with the ligand on the membrane pore surface and is subsequently displaced in a concentrated state.

In any pressure driven process with a polymeric material or suspension, a process known as concentration polarization occurs which results in substantial loss of permeation due to fouling of the membrane surface. This phenomenon limits the concentration of polymer or suspended absorbent which can be efficiently used. Inasmuch as the invention described here does not require a significant transmembrane pressure or liquid flux across the membrane, this polarization or fouling process will not occur.

An additional means of selective extraction using membranes involves the use of a selective solvent extractant, immiscible with both the feed solution and the liquid product stream, which is imbibed into the pores of a porous membrane. These systems are prone to loss of selectivity due to excessive transmembrane pressure, forcing the organic solvent out of the pores and developing a leak across the membrane. Another common problem is the maintenance of the solvent in such a small volume relative to the flow streams on both sides of the membranes and also, the slight solubility of the extractant and solvent in the effluent streams requires periodic replacement of either the extractant fluid or the entire membrane itself. The subject invention does not involve a selective membrane or solvent, but instead a selective polymer and minimal losses thereof can easily be replaced in a continuous flow loop during normal operation as necessary.

Despite the widespread existence of different processes for the selective extraction of various materials, the art has not recognized heretofore a process wherein a permeable membrane is employed in conjunction with a particular affinity adsorbent that has a binding affinity for the material to be removed. As a result, the process of the present invention does not require chelating ion-exchange resins, which are difficult to manufacture; physical attrition of resin beads is avoided; and, there is no loss of polluting solvents or expensive extractants which characterizes solvent extraction and liquid filled selective membrane processes.

SUMMARY OF THE INVENTION

In general, the process of the present invention for the selective dialysis of liquid streams containing different materials comprises the steps of providing a porous membrane in a cell, which membrane has pores of sufficient dimension to allow passage of different materials therethrough, and then circulating an affinity adsorbent stream against a first side of the membrane wherein the adsorbent has a dimension larger than that of pores and has a preferred binding capacity for at least one but not all of the different materials. The process continues by passing the liquid stream containing the different materials against a second side of the membrane whereby certain of the materials become bound to the affinity adsorbent upon passing through the membrane to the first side thereof in a concentration greater than their concentration in the liquid stream and become separated from others of the materials which can return to the second side of the membrane.

The dialysis process can optionally be employed with additional steps which include stripping the bound material from the affinity adsorbent; scrubbing the affinity adsorbent stream containing different materials bound in greater and lesser states of concentration thereto than their respective concentrations in the liquid stream and containing some unbound materials and, regenerating the affinity adsorbent stream.

The stripping process can be employed separately with other types of feed streams other than those resulting from the dialysis process. Such streams as comprise an adsorbent or chelating material loaded with one or more materials are separated in a cell having a membrane. The process includes the steps of providing a porous membrane in a cell, the membrane having pores of sufficient dimension to allow passage of the different materials therethrough; circulating a stripper reagent against a first side of the membrane; passing the adsorbent material containing one or more bound materials against a second side of the membrane whereby upon contacting the stripper reagent, the bound material is released from the adsorbent and passes through the membrane to the first side and out of the cell at one end while the stripped adsorbent passes out of the cell at a second end. The stripping process can itself be employed with separate steps of scrubbing and regeneration.

PREFERRED MODE FOR CARRYING OUT THE INVENTION

As noted hereinabove, practice of the process of this invention requires two components—a porous membrane and an affinity adsorbent which is selected for its preferred affinity to chelate or otherwise combine with the material or materials that are to be separated from other material or materials in a liquid flow stream. The process is particularly suitable for counter current mode operation where the feed stream laden with a mixture of materials is passed through the membrane device such as, for instance, through the lumen of a bundle of hollow fibers, and the affinity adsorbent is outside the fibers, flowing in the opposite direction, typically in reduced volume compared to the feed or vice-versa. Materials from the feed stream diffuse freely through the membrane pores; those that chelate with the affinity adsorbent cannot return and remain outside of the membrane. The affinity adsorbent exits carrying a large concentration of at least one material, the concentration of which is significantly lowered in the feed stream.

More particularly, where there are two materials in the liquid stream, such as copper and zinc, that are different but present in approximately similar concentrations and an affinity adsorbent is selected having a greater affinity for copper than zinc, e.g., 9:1, then the concentration of the bound materials to the affinity adsorbent will be on the order of 90% copper and 10% zinc. The copper will thus be the material in greater concentration and zinc will be in lesser concentration. In some systems it may be possible to concentrate or bind exclusively one material versus another, but the process is indeed useful if at least one can be greatly concentrated over the other(s) as compared to the initial concentrations in the liquid feed stream.

Figure 1:
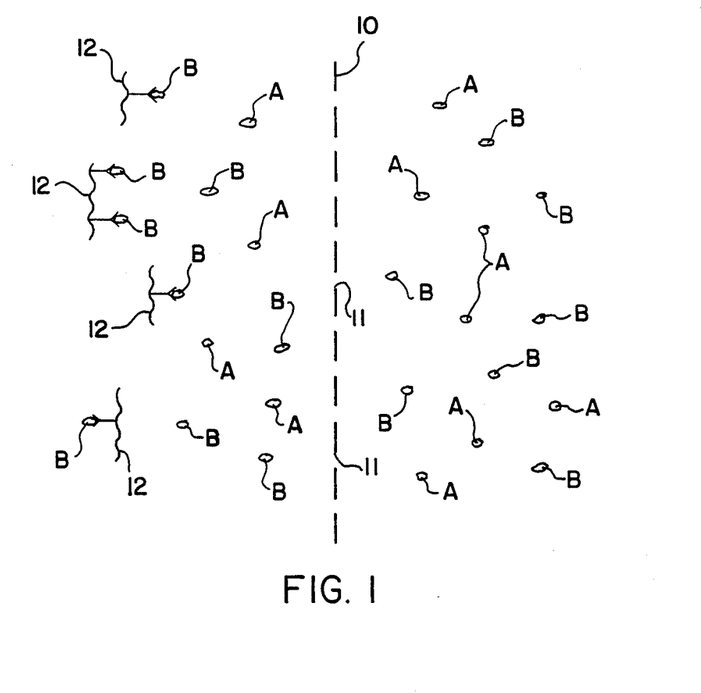
FIG. 1 schematically depicts the operation of the dialysis process of the present invention.

With reference to FIG. 1, it will be noted that the dialysis process of the present invention employs a semipermeable membrane 10, having a plurality of pores 11. The feed stream contains particles of different materials A and B, both of which can pass freely through pores 11. This feed stream is circulated on one side of the membrane. On the other side is circulated the affinity adsorbent, with several polymer chains being designated for instance and referenced by the numeral 12. The polymer adsorbent has been selected as having a chelating or other binding ability for the B material which can no longer pass freely back through the membrane 10. The A material, on the other hand, can return and eventually is separated from the B material. The polymer adsorbent can thereafter separately be treated to strip the B material after which it can be regenerated and returned for continued use as the adsorbent.

Several requirements exist for the membranes utilized in this process. They must be substantially impermeable to the affinity adsorbent extractant, they must be substantially permeable to the desired materials being extracted, and they must also be relatively chemically and physically stable in the process streams being treated. The desired membranes should also not be strong adsorbents of either the adsorbed species or the adsorbent being used. Typical dialysis membranes such as those commonly used in artificial kidneys are good examples of membranes suitable for this process. Such membranes can be made from a variety of polymers including, but not restricted to, cellulosics including regenerated cellulose, polyphenylene oxides, polysulfones, polyvinylidine halides, polyolefins, polycarbonates, polyimides, polyvinyl alcohol, fluorocarbon polymers, polyacrylonitrile and common substituted analogs thereof as well as copolymers of any of the foregoing. The form of membrane selected does not constitute a limitation of the process inasmuch as both hollow fibers and flat sheets can be employed.

Similarly, a wide variety of adsorbent materials may be utilized for practice of the subject invention. Requirements for these materials are that they be too high in molecular weight to diffuse readily through the membrane and that they have a selective affinity for at least one species over another, both of which species will diffuse through the membrane. The adsorbent material may be soluble in, suspended in or otherwise carried along by the fluid on the product side of the membrane and should be capable of being stripped of the desired species by one of several means.

For example, the adsorbent solution may be used without further treatment as feed to a conventional recovery system such as a roaster for metals beneficiation, or it may be treated with chemicals, heat, pH change, electrolytic means or other means to destroy the complex formed and then the desired materials are separated by conventional means or by use of another membrane step, either dialysis or ultrafiltration.

In complex systems of feed components, multiple adsorbents may be used in the same unit to extract several desirable materials which may then be easily separated by those techniques mentioned above, particularly where significant concentration is achieved. Alternatively, appropriately designed adsorbents may selectively release their bound materials under different conditions such as pH thereby effecting a further separation. Such an enhanced separation may also be possible in this invention with a generally selective adsorbent which can be induced to release its complexed material selectively.

Example materials for adsorbents include six classes of materials: chelating or ion exchange polymers; biological polymers and cells that are highly selective to binding small molecules such as organic materials; ground small particle ion exchange resins; activated charcoal; natural and synthetic ion exchange materials; and, enzymes which utilize as co-factors certain organic compounds. Exemplary ion exchange polymers include sulfonated polyolefins, polyethylenimine, polyacrylic acid based compounds, chelating polymers known to the art and envisioned based on known chelation behavior and known polymer backbones.

Ion exchange resins are well known, one typical example being exemplified hereinbelow. These are preferably ground to a small particle size to increase surface area but not as small as to be able to pass through the pores of the membrane employed. Where a hollow fiber polymer membrane is employed, the resins should be ground to at least 0.1 of the diameter of the fiber lumen. Suitable resins for this purpose include XFS 43084 and XFS 4196 from Dow Chemical. Both are based on picolylamine (2-aminomethylpyridine) and are described as macroporous polystyrene/divinylbenzene copolymers to which has been attached a chelating functional group. Their structures are as follows:

XFS 4196
N-(2-hydroxyethyl)-picolylamine
HEPA

XFS 43084
N-(2-hydroxypropyl)-picolylamine
HPPA

Most of the foregoing affinity adsorbents are water soluble materials but practice of the present invention does not necessarily exclude either insoluble materials such as finely divided ion exchange resins, activated charcoal and natural and synthetic ion exchange resins or materials used in nonaqueous systems to which the dialysis process described herein may be applicable.

The adsorbent material is carried by a solvent which is either water or a nonaqueous, organic media such as alcohols, aromatic solvents or chlorinated solvents, although water is preferred due to its availability and the fact that it is not likely to pollute as would an organic solvent. Where an organic solvent is employed, e.g., separation of amino acids which are soluble in alcohol, the alcohol solvent must be capable of solvating or suspending the adsorbent but not dissolving the membrane. The adsorbent is generally dissolved in the solvent to a maximum concentration which will vary as the adsorbent and solvent vary, as well as practical limitations due to viscosity. Inasmuch as the process of the present invention is not based on or related to solvent extraction, it will be understood that the solvent carrier of the feed stream is approximately the same as the solvent for the adsorbent which is to say they are not immiscible.

The type of materials that can be removed or extracted by the dialysis process of this invention includes ionic species, both anions and cations, and organic species such as organic and biological solutes. More particularly, substantially any anions such as carboxylates, chromates, nickel, zinc or gold cyanide complexes from plating wastes and the like can be treated to extract selected materials; cations as well, particularly transition metal ions, as may be present in common plating wastes, e.g., nickel or zinc ions, rare earth metals, metals in photographic processes, liquors from mining operations and many others can also be treated to extract specific metals. A wide variety of organic and biological materials can also be treated including amino acids, sugars, optical isomers, fuels and the like contaminated with salts, water or other impurities.

The term different materials is employed herein to connote differences in species, e.g., copper from zinc; chromate from chloride as well as differences in genuses, e.g., water or salts from organic fuel and should be understood to mean that in any combination of two or more materials, at least one material can be extracted or separated from another in a stream where both are present. It is to be understood that practice of the present invention does not require the use of any specific affinity adsorbent material; polymer, ion exchange resin or enzyme; semipermeable membrane or solvent or combination thereof that would be universal for ionic species as well as organic. On the contrary, an advantage of the process is that selection of any one or more of these three variables can be tailored exactly to the separation that is desired, taking into account the composition of the feedstream.

A brief summary of the range of physical characteristics within which the process of this invention is believed to be applicable is set forth in Table I.

TABLE I

Conditions for Practice of Affinity Dialysis Process

| Component | Form | Determining Characteristic | Broad Range | Preferred Range |
|---|---|---|---|---|
| Adsorbent | Polymeric | Mw[a] | 3K[b] to 3 Million | 5K to 50K |
| Adsorbent | Solid - Susp. | Size | 0.01 to 5 Micron | 0.1 to 0.5 |
| Membrane | Porous | Mw Cutoff | 1000 to Solids | 2K to 10K |
| Solvent | Liquid | Type | $H_2O$ or Organic | Aqueous |
| Adsorbant | Dissolved | Type | Ionic to Organic | Ionic |
| Adsorbant | Dissolved | Mw | 18 to 50K | 40 to 1000 |

[a] Molecular weight
[b] × 1000

In the exemplary work reported hereinbelow the dialysis process of the present invention was practiced utilizing both hollow fiber and flat sheet semipermeable membranes and two different polymer adsorbents for the extraction of cations, e.g., calcium and copper, and anions, namely chromate. Several of the procedures have been set forth with a brief discussion of the apparatus employed.

Hollow fiber units normally provided as artificial kidneys by Travenol Laboratories, Inc. as CF Model 12*11 were disassembled and the hollow fibers removed to provide a source to manufacture small tube-in-shell units. The fibers were manufactured from regenerated cellulose. The hollow fiber units which had 316 stainless steel cases, contained 150 square cm of membrane (170 fibers), and had tubesheets made of Dow Corning RTV silicone adhesive. Hollow fiber membranes were flushed by pumping distilled water through both sides of the fiber units for 10 minutes prior to use and were kept wet thereafter. All membranes and membrane units were stored in a preservative of 2 percent formaldehyde when not in use.

Figure 2:
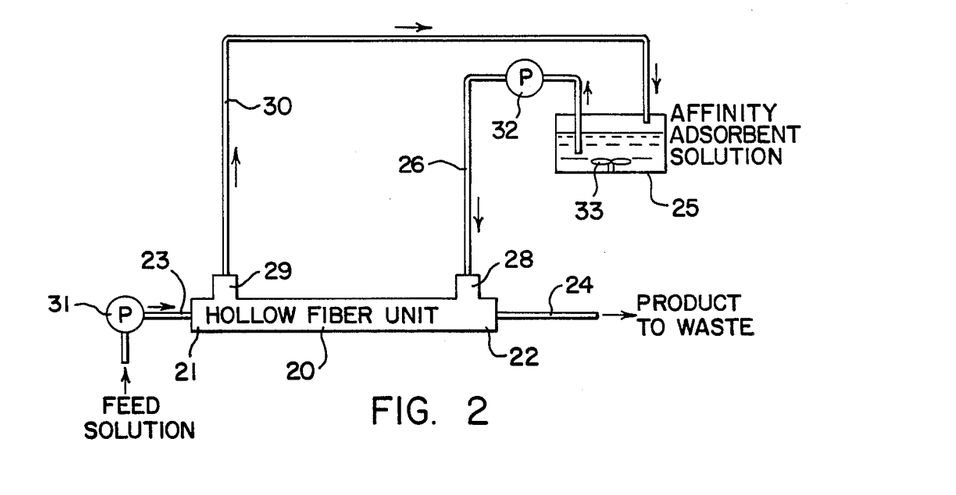
FIG. 2 is a diagrammatic view of a mode for conducting the dialysis process of the present invention, employing hollow fibers and a recirculation.

Initial work was conducted utilizing the system schematically depicted in FIG. 2 which provides a hollow fiber unit 20 of stainless steel or other suitable material within which is enclosed hollow fibers (not shown) of semipermeable membrane. Inlet and outlet ends, 21 and 22, respectively, are provided through which the feed solution is fed (line 23) and the stripped solution exits (line 24).

The adsorbent polymer solution or other affinity adsorbent is fed from a reservoir 25 to the unit 20 through line 26 and port 28 where it is driven countercurrent through the unit 20 to exit at port 29 near feed inlet 21. The adsorbent solution is recycled through line 30 to the reservoir until it is eventually laden with the materials for which it is selective at which time a separation step can be employed as will be discussed in greater detail hereinbelow. Pumps 31 and 32 can be employed to move the feed solution and polymer solution and the latter may be stirred during circulation via driven impeller 33.

As is evident from FIG. 2, the feed solution was flowing single pass countercurrent to the polymer solution which was recycled to ensure maximal loading of the polymer with the desired extractable species. Typically a multichannel peristaltic pump (not shown) such as an Ismatec IPS was used to provide flow on both sides of the membrane. For several of the experiments, a back pressure device was installed on the outlet polymer stream to apply a variable pressure, i.e., 10 psi (0.07 MPa), to that side of the membrane. That pressure was sufficient to offset the tendency for the polymer to draw water through the membrane via osmosis (or more correctly oncosis in the case of polymers).

Figure 3:
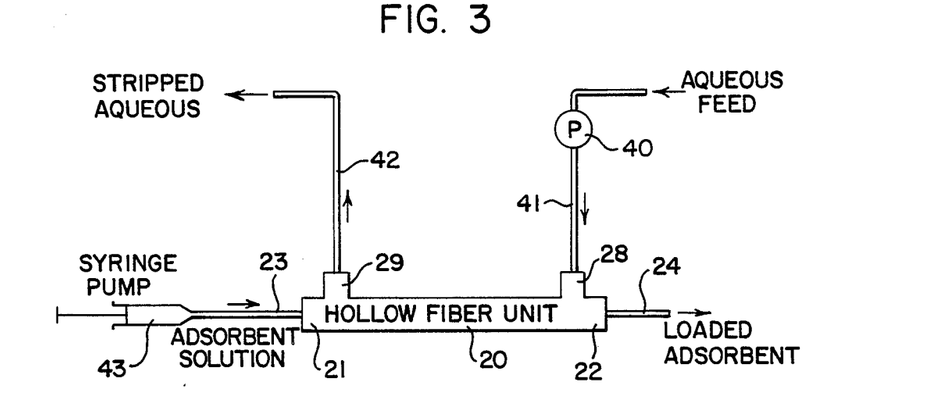
FIG. 3 is a diagrammatic view of a continuous counter current mode for conducting the dialysis process of the present invention, employing hollow fibers.

FIG. 3 depicts an apparatus for continuous countercurrent mode work that was also employed for longer term steady state work. The apparatus included a similar hollow fiber unit 10 as described in conjunction with FIG. 2. The polymer adsorbent was fed via pump 40 and line 41 into port 28 and allowed to exit at port 29 through line 42 to a separate stripping operation. Although not shown, the peristaltic pump used previously was used for pumping the feed through the shell of the hollow fiber units and a Sage syringe infusion pump, 43, was used to pump polymer solution through the inside of the fibers at a slow, controlled rate. Periodic samples of the polymer solution and the treated feed were analyzed to determine treatment efficiency and stability of the system.

Finally, experiments with flat membranes were conducted using a modified Amicon CEC-1 cell or a stainless steel version of that unit. These were modified to allow for flow on both sides of the membrane. The membrane utilized was Spectrapore 5000 molecular weight cutoff flat cellulose film. The membrane was prepared by submersion in running water for ten minutes prior to use and was kept wet after initial wetting.

The dialysis process just described can be combined with a strip stage at which the material or materials bound to the affinity adsorbent can be removed. Further and optionally, a scrub stage can be employed for pre-treating the loaded affinity adsorbent prior to stripping and lastly, the process can employ a step of regenerating the adsorbent prior to its re-use in the extraction stage.

Figure 4:
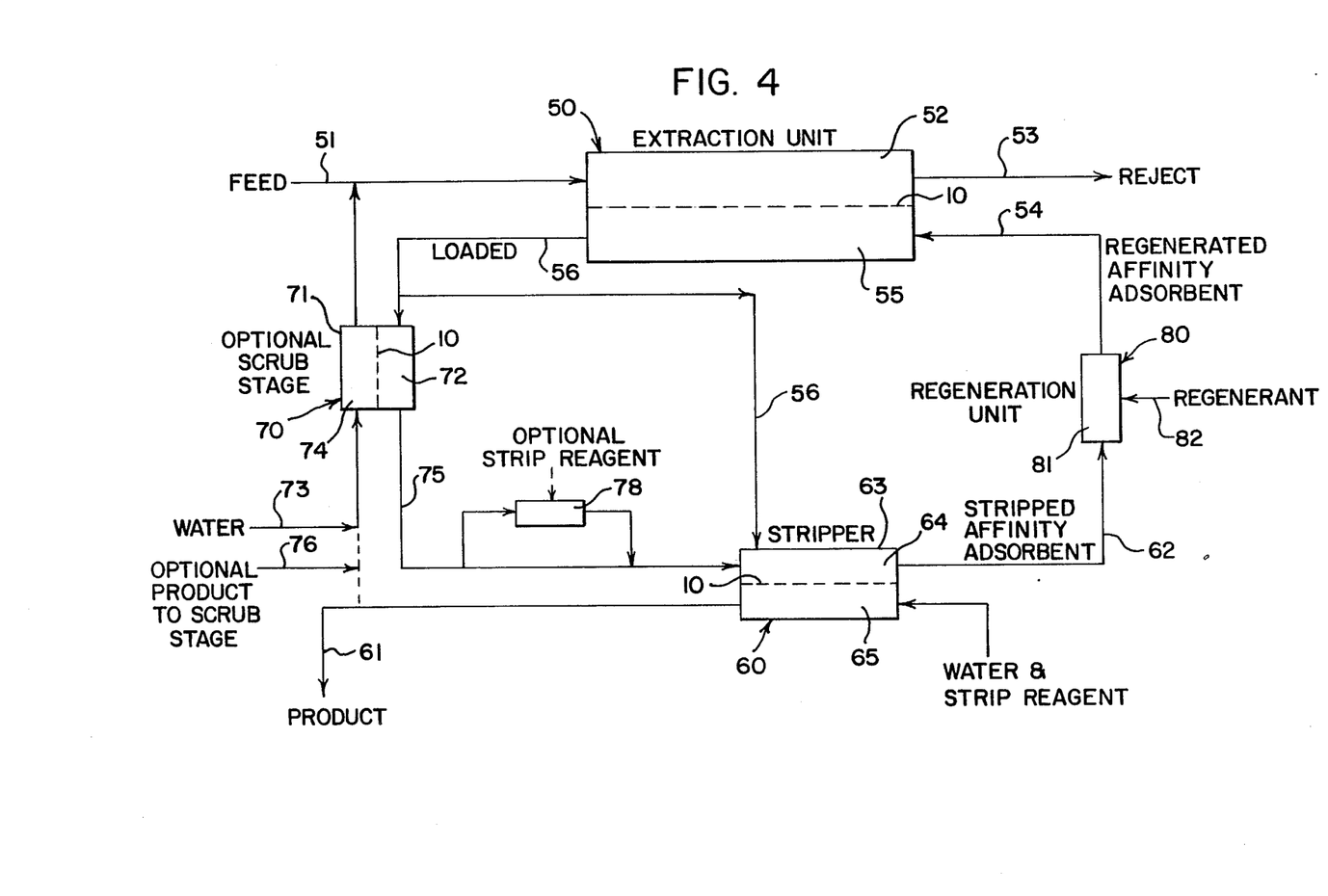
FIG. 4 is a schematic diagram of the dialysis process of the present invention along with separate processes for stripping, scrubbing and regenerating that can be employed in various combinations with and without the dialysis process.

With reference now to FIG. 4, the description of the additional stages shall proceed. The drawing depicts schematically four separate stages as follows: extraction, indicated generally by the numeral 50; stripping, indicated generally by the numeral 60; scrubbing, indicated generally by the numeral 70; and regenerating, indicated generally by the numeral 80. The extraction unit 50 constitutes the main process of the present invention. It employs a membrane 10, a feed 51 of different materials circulated against one side 52 of the membrane; an effluent stream 53, essentially stripped of at least one of the different materials; a supply of the affinity adsorbent 54, either fresh or regenerated and circulated against a second side 55 of the membrane; and a stream of loaded affinity adsorbent 56. This process having been detailed hereinabove, further discussion shall not be repeated.

While the extraction or dialysis process constitutes the basic invention, in those instances where a cyclic process is desired, the different material that is extracted can be stripped from the stream 54 in stripper 60 providing a product 61 or concentrated material from feed 51 and an unloaded affinity adsorbent, stream 62. The stripper unit 63 comprises a cell or hollow fiber unit similar to the unit 20 described in FIG. 2, although a counter-current flow is not necessarily mandatory. The cell 63 is provided with a membrane 10 such as described hereinabove and it is to be noted that the extraction unit 50 and stripper unit 60 can employ the same or different membrane materials.

The loaded adsorbent 54 is passed against a first side 64 of the membrane while a strip reagent, which is usually aqueous, is passed against a second side 65 of the membrane 10. In the instance where one or more metals have been extracted, they may be separated readily by $Cu^{2+}$ ions in solution which will form a much stronger complex with the affinity adsorbent. The generation provides that the $Cu^{2+}$ ions will pass through the membrane pores, exchange the cation(s) held by the adsorbent which then pass through the pores and out of the cell 60 as a product stream 61, e.g., as a metal chloride or other salt.

When copper or other cations have been extracted, the strip reagent comprises an aqueous inorganic acid, e.g., hydrochloric, nitric, sulfuric and the like. By lowering the pH to about 4 or lower and preferably to a range of between 1 to 2, the complex will be destroyed and the metal(s) extracted will be released. Again the freed material, metallic chloride, nitrate, sulfate and the like will flow out via product stream 61 and the stripped adsorbent flow via stream 62. Acid addition can be effected separately where the initial complex was first treated with $Cu^{2+}$ ions.

Assuming next than an anion were extracted, e.g., $CrO_4^{2-}$, the strip reagent should comprise a base such as aqueous sodium hydroxide to raise the pH of the adsorbent/complex stream to at least 8 and up to about 10 or higher. Lastly, where an organic species was extracted, these complexes can be destroyed also by the addition of a strip reagent which will be either a suitable acid or perhaps a competitive inhibitor where the affinity adsorbent is an enzyme for a particular material in the feed stream 51.

It is to be understood that the selection of a particular stripper reagent should not constitute a limitation on the present invention inasmuch as the stripper can be selected not only to match a particular affinity adsorbent/complex stream but also to provide a particular product stream that may, in turn, constitute a useful, saleable material or one that can be discarded harmlessly or that may be suitable for further processing beyond the scope of the present invention. Furthermore, although the stripping stage 60 has been described in conjunction with the extraction stage 50, it should be understood that the stripping process just described may well provide a separate invention for the stripping of a material or materials from a complex as where stream 54 originated elsewhere, as a feed to the cell 63, rather than the effluent from a dialysis unit.

As a further optional step, either to the dialysis process conducted in unit 50 with the stripping step, unit 60, or where stripping is conducted as a separate process, the scrubbing stage 70 can be employed. The scrubbing unit 70 also can comprise a cell or hollow fiber unit 71 not unlike cells 20 and 63, referenced hereinabove. The cell 71 also employs a membrane 10 that can be the same or different membrane as employed in the other cells. The purpose of the scrubbing stage is to increase the proportion of product material desired in product stream 61, thereby making the stripping process more efficient.

In operation, the loaded adsorbent/complex stream 54 is fed to a first side 72 of the membrane 10 and a stream of water 73 is fed to the second side 74. The purpose of the water feed is to remove any extraneous material that is first soluble and second not complexed with the adsorbent so that the effluent complex stream 75 can be fed directly to stripping stage 60 and the resultant product stream 61 will be free thereof.

As a further step the scrubbing stage may provide for the addition of separate stream 76 of the product in stream 61. By way of explanation, let it be assumed that the original feed contains a 50/50 concentration of materials A and B and that the affinity adsorbent selected complexes both A and B in a ratio of 10 parts A to 90 parts B which will be the concentration of A and B in stream 54. If stream 76 provides a 5% concentration of the B material, then inside of cell 71, a corresponding amount of A material will be displaced from the adsorbent effecting a 50% reduction of the unwanted A material and therefore the composition of stream 75 will be 95 parts B to 5 parts A.

If it be further desired to concentrate the feed to stripper 60, an optional pre-stripping stage 78 can be employed in stream 75 where a stripper reagent is added either as a mixing stage for ultimate stripping at 60 or to remove the A material from the preceding example in the manner as was described hereinabove for the stripping stage 60.

Lastly, the stream 62 from the stripping stage 60 can be fed to the regenerating stage 80 which comprises a vessel 81 to which a regenerant stream 82 is fed. It will be recalled that for cation removal in stripping unit 60 an inorganic acid was added to destroy the complex. Then, in regenerating stage 80 a base would be added as the regenerant to re-adjust the pH and ready the affinity adsorbent for further complexing as it is returned to extraction unit 50 via stream 53. In similar manner, the regenerant can comprise an acid or other material, depending upon the stripping reagent employed in the preceding step.

Recapitulating, it should be clear that the dialysis process of the present invention is based solely on the extraction step employing an affinity adsorbent and that the additional steps discussed in conjunction with FIG. 4 are optional. One of these, the stripping process depicted by unit 60 is also novel and can be employed without the extraction step and with or without the additional steps of scrubbing and regenerating.

It is to be understood that practice of the present invention is not limited to any of the units depicted in the drawings or otherwise discussed herein. Rather, these have been described only to detail the exemplification provided hereinbelow.

CATION EXTRACTION

In the work which is reported next, cation extractions, namely Ca(II), Cu(II), Fe(II) and Fe(III) were conducted. Analyses for calcium ions were performed by EDTA titration using a Hach Co. calcium analysis kit while colorimetric methods for Cu(II), Fe(II) and Fe(III), and Cr(VI), also obtained from Hach, were employed to allow monitoring of these ions on a semi-continuous basis. Final samples of polymer solution, feed and reject were submitted for PES analysis as a confirmation of the colorimetric and titration results as well as for sodium and potassium where appropriate. Chloride samples were also analyzed. Adjustment of pH was with the aid of an Orion pH meter calibrated at pH 7.00 with standard buffer. Extraction polymers employed as affinity adsorbents included poly(2-acrylamido2-methylpropanesulfonic acid), (polyAAMPS) or polyethylenimine (PEI). A separate extraction employing ground ion exchange resin as the affinity adsorbent is also reported as is a biological extraction employing an enzyme.

EXAMPLE NO. 1

A 2.5% solution of polyAAMPS in water was prepared, 50 ml of which were employed. After adjusting the solution pH to 7 with 50% sodium hydroxide, a hollow fiber unit as set forth in FIG. 2, containing Travenol hollow fibers, was employed to expose the polymer solution to a feed stream of 160 ppm calcium as calcium ion. The feed stream was pumped through the fiber lumen at a rate of 0.70 ml/min and the polymer solution recirculated through the shell at 4.0 ml/min. The volume of the polymer solution increased from 50 ml to 70 ml over the course of the 30 hour evaluation. The polymer concentration at termination of the experiment was 3000 ppm calcium ion while the effluent concentration was 11 ppm yielding a concentration factor of polymer/effluent of 273. Calculated selectivity for Ca/Na was 39 based on the final concentrations of those species in the effluent and in the polymer solution. Calcium permeability through the membrane varied from $2.4 \times 10E^{-2}$ to $1.1 \times 10E^{-2}$ cm/min at the start and termination of the experiment, respectively. These values are consistent with the permeability obtained on aqueous solutions of calcium chloride. Calcium extraction, as a function of time appears in Table II.

TABLE II

| Selective Removal of Ca with PolyAAMPS | | |
|---|---|---|
| Time (hrs) | Ca conc in feed[a] (ppm) | Ca conc in polymer[a] (ppm) |
| 0 | 160 | 0 |
| 1 | 10 | 100 |
| 2 | 6 | 200 |
| 4 | 2 | 500 |
| 8 | 2 | 750 |
| 12 | 2 | 1300 |
| 16 | 3 | 1600 |
| 20 | 6 | 2000 |
| 24 | 8 | 2450 |
| 28 | 10 | 3000 |

[a]As Ca

EXAMPLE NO. 2

In this instance, a calcium chloride/sodium chloride solution was employed having a concentration of 400 ppm each. The polymer solution was the same as in the prior experiment except that pH was adjusted to 6.67. After eight hours with similar flow rates but with the higher calcium concentration, the amount of calcium in the polymer was over 8500 ppm as calcium ion. Selectivity for Ca/Na was 25 on a molar basis and loading of the polymer was 69% calcium and 31% sodium at the conclusion. The concentration factor of calcium was 50 fold for polymer over feed. Calculated membrane permeability for calcium was in the $9 \times 10E^{-3}$ range. Removal of calcium from sodium over eight hours appears in TABLE III.

TABLE III

| Removal of Ca from Na with PolyAAMPS | | |
|---|---|---|
| Time (hrs) | Ca conc in feed[a] (ppm) | Ca conc in polymer[a] (ppm) |
| 0 | 170 | 0 |
| 1 | 100 | 1000 |
| 2 | 25 | 2000 |
| 3 | 25 | 2250 |
| 4 | 28 | 2500 |
| 5 | 28 | 2900 |
| 6 | 30 | 3500 |
| 7 | 50 | 4500 |
| 8 | 60 | 8100 |

[a]As Ca

It is clear from Examples 1 and 2 that an unexpectedly high degree of selectivity for calcium over sodium was observed. The selectivity calculated for the experiments averaged 32 for Ca/Na, much higher than the value observed for typical sulfonate ion exchange resins which averages 2.6. An additional advantage of the process of this invention is the high permeability coefficients that have been observed even in the presence of a relatively high polymer concentration which is strong evidence of the absence of fouling of the membrane by the polymer. Actual mass transfer is higher in the polymer system than with water as dialysate even though the diffusion coefficients are similar, due to the assumption made in the calculations that the polymer side concentration for free calcium is zero, further assuming the bound calcium is in an infinite sink and no longer interacts. Hence, in the presence of the polymer the removal of calcium is actually greater.

EXAMPLE NO. 3

The extraction of Cu(II) was next studied both from an aqueous solution of copper sulfate and from a mixture of copper and iron(II) sulfates. In Example No. 3, an equilibrium study, 2.5 ml of 5% PEI in water were placed into the lumen of a small bundle of Spectrapore hollow fibers and 1000 ml of 118 mM Cu(II) and 64 mM Fe(II) was circulated around the outside of the fibers for 4 hours. At that time the two solutions were analyzed for Cu and Fe content. Table IV presents the results of this extraction.

TABLE IV

Extraction of Copper from Copper (II)/Iron (II) with PEI

|  | Polymer (at Equilibrium) | Feed (at Equilibrium) |
|---|---|---|
| $Cu^{+2}$ (Total) | 200 mM | 118 mM |
| $Fe^{+2}$ (Total) | 68 mM | 64 mM |
| $Cu^{+2}$ Bound to Polymer | 82 mM | — |
| Free $Cu^{+2}$ | 118 mM | 118 mM |
| $Fe^{+2}$ Bound to Polymer | 4 mM | — |
| $Fe^{+2}$ Free | 64 mM | 64 mM |

Selectivity for Cu(II) in the foregoing example was 10.8. Selectivity can be defined as:

$$S_{a/b} = \frac{[a \text{ bound}]}{[a \text{ free}]} \cdot \frac{[b \text{ free}]}{[b \text{ bound}]}$$

In lower feed concentration example selectivity was typically 10.5 to 11 for Cu(II)/Fe(II) and concentration factors of up to 236 were achieved for copper.

EXAMPLE NO. 4

Example No. 4 was conducted using a system similar to that used with the Ca/Na - polyAAMPS work described hereinabove and shown in FIG. 2. Polymer solution was flowing on the shell side at 3.0 cc/mn. Results are reported in Table V of a polymer (polyAAMPS) concentration of 2.5%, pH 6.7 and a volume of 25 ml. The polymer was recycled at 2.7 cc/min. Feed concentration of copper was 330 ppm as copper sulfate with a feed flow of 0.75 ml/min. The copper concentration continued to increase to a maximum of 11,550 ppm over a period of 7.5 hours.

TABLE V

Copper Extraction with PolyAAMPS

| Time (hrs) | Cu conc in feed[a] (ppm) | Cu conc in polymer[a] (ppm) |
|---|---|---|
| 0 | 330 | 0 |
| 1 | 98 | 190 |
| 2 | 0 | 420 |
| 3 | 0 | 2540 |
| 4 | 0 | 3680 |
| 5 | 6 | 5080 |
| 6 | 9 | 7300 |
| 7 | 10 | 11550 |
| 7.5 | 13 | 11550 |

[a]As $CuSO_4$

EXAMPLE NO. 5

Example No. 5 was also conducted with copper and polyAAMPS but using an Amicon VITAFIBER cell culture tube Model PM10 with polysulfone hollow fibers having a nominal 10,000 molecular weight cutoff. A key result of this example was a dramatic increase in the copper permeability through the membrane when the polymer was used. With a dialysate of water, the copper permeability was $2 \times 10E^{-3}$ cm/min while with the polymer as the dialysate, the permeability increased to $1.5 \times 10E^{-2}$. Feed flow was 0.5 cc/min. A 2.5% polyAAMPS polymer was employed; pH 6.7, recycle rate 2 cc/min. Results are reported in Table VI.

TABLE VI

Copper Extraction with PolyAAMPS and Amicon Unit

| Time (hrs) | Cu conc in feed[a] (ppm) | Cu conc in polymer[a] (ppm) |
|---|---|---|
| 0 | 330 | 0 |
| 1 | 40 | 305 |
| 2 | 20 | 430 |
| 3 | 20 | 1800 |
| 4 | 20 | 2280 |
| 5 | 10 | 3080 |
| 6 | 18 | 3550 |
| 22 | 203 | 19140 |

[a]As $CuSO_4$

EXAMPLE NO. 6

Similar results are reported in Table VII where the same feed as was used with Example No. 5 was fed to the same Amicon Unit but 5% PEI was used instead of polyAAMPS. Over a 95 hour period, a copper concentration of 8900 ppm was reached but the rate of transfer and the maximum concentration achieved was less than that observed in the polyAAMPS example. The permeability rates with the polymer in the system were somewhat higher than those for water alone as the dialysate. Feed flow was again 0.5 cc/min. The polymer was recycled at 2.7 cc/min.

TABLE VII

Copper Extraction with PEI and Amicon Unit

| Time (hrs) | Cu conc in feed[a] (ppm) | Cu conc in polymer[a] (ppm) |
|---|---|---|
| 0 | 330 | 0 |
| 10 | 72 | 172 |
| 20 | 230 | 2280 |
| 30 | 240 | 3000 |
| 95 | 290 | 8900 |

[a]As $CuSO_4$

EXAMPLE NOS. 6-9

Several experiments were performed using the modified Amicon CEC-1 thin channel unit. The membranes used were Spectrapore 5000 molecular weight cutoff cellulose films. These examples demonstrate the efficacy of using flat film membranes for the process of the present invention where polymers and feed stream similar to those discussed above are employed. The results of the flat membrane studies are presented in Table VIII and although the results successfully prove the concept, the work was more difficult to control, much slower due to smaller membrane area, and required much closer monitoring of conditions.

TABLE VIII

Flat Membranes in the CEC-1 Cell

| Ex. No. | Feed Flow (cc/min) | Polymer Flow[a] (cc/min) | Polymer | Feed (ppm) | K cm/min |
|---|---|---|---|---|---|
| 6 | 0.25 | 0.95 | 2.5% AAMPS | 400 $CuCl_2$ | $1.4 \times 10^{-3}$ |
| 7 | 0.25 | 1.05 | 5% PEI | 400 $CuSO_4$ | $0.8 \times 10^{-3}$ |
| 8 | 0.50 | 0.50 | 2.5% PEI | 400 $CuSO_4$ | $0.8 \times 10^{-3}$ |
| 9 | 0.25 | 1.0[b] | $H_2O$ | 400 $CaCl_2$ | $1.3 \times 10^{-3}$ |

[a]Recycled
[b]Not recycled

EXAMPLE NOS. 10–16

The next seven examples were conducted with the system depicted in FIG. 3, continuous countercurrent extraction, which is believed to be the most probable mode of operation of the process of the dialysis invention. These examples were run at various feed and polymer flow rates using a system of 2.5% polyAAMPS and 400 ppm calcium chloride with polyAAMPS, adjusted to pH 6.7 as hereinbefore. The results of six continuous extractions with polyAAMPS are reported in Table IX. For comparison, Example No. 16 was conducted without any polymer. Typically, an increase in feed flow resulted in an increase in polymer steady state calcium concentration as did a decrease in polymer flow.

TABLE IX

Continuous Counter Current Flow With Feed of 400 ppm Calcium Chloride and 2.5% PolyAAMPS

| Ex. No. | Feed Flow (cc/min) | Polymer Flow (cc/min) | % CaCl₂ Removed | CaCl₂ in Polymer (ppm) | K cm/min |
|---|---|---|---|---|---|
| 10 | 2.0  | 0.36     | 94% | 2,700 | $3.8 \times 10^{-2}$ |
| 11 | 2.07 | 0.24     | 94% | 3,190 | $3.8 \times 10^{-2}$ |
| 12 | 2.04 | 0.11     | 74% | 4,910 | $1.3 \times 10^{-2}$ |
| 13 | 1.07 | 0.21     | 97% | 2,700 | $2.65 \times 10^{-2}$ |
| 14 | 1.03 | 0.14     | 92% | 3,750 | $1.7 \times 10^{-2}$ |
| 15 | 1.04 | 0.06     | 41% | 2,600 | $0.4 \times 10^{-2}$ |
| 16 | 1.06 | 5.20[a]  | 75% | —     | $1.46 \times 10^{-2}$ |

[a]No polymer

EXAMPLE NOS. 17–18

Calcium removal with polyAAMPS in a continuous countercurrent flow was conducted and monitored for two additional examples. Calcium removal with 2.5% polyAAMPS, pH 6.7, feed flow 1.00 cc/min, polymer flow 0.12 cc/min is reported in Table X and at a feed flow 2.1 cc/min, polymer flow 0.23 cc/min is reported in Table XI.

TABLE X

Calcium Removal with PolyAAMPS Continuous Countercurrent Flow - Ex. 17

| Time (hrs) | Ca conc in effluent[a] (ppm) | Ca conc in polymer[a] (ppm) |
|---|---|---|
| 0 | 165 | 0 |
| 1 | 8   | 840 |
| 2 | 11  | 1490 |
| 3 | 12  | 1540 |
| 4 | 20  | 1450 |
| 5 | 18  | 1590 |
| 6 | 16  | 1560 |
| 7 | 15  | 1620 |

[a]As Ca

TABLE XI

Calcium Removal with PolyAAMPS Continuous Countercurrent Flow - Ex. 18

| Time (hrs) | Ca conc in effluent[a] (ppm) | Ca conc in polymer[a] (ppm) |
|---|---|---|
| 0 | 168 | 0 |
| 1 | 15  | 1680 |
| 2 | 13  | 1550 |
| 3 | 13  | 1200 |
| 4 | 11  | 990 |
| 5 | 9   | 1080 |
| 6 | 9   | 1090 |
| 7 | 9   | 1500 |
| 8 | 9   | 1250 |
| 9 | 10  | 1250 |

[a]As Ca

Anion Extraction

EXAMPLE NOS. 19–20

In order to demonstrate the efficacy of the process of the present invention for the extraction of anions, 5% PEI in water was employed as the extractant for chromate ion. Twenty five ml of the 5% PEI was recirculated at 3 ml/min on the outside of one of the standard 150 square cm hollow fiber units while 1.0 ml/min of a solution of 400 ppm potassium chromate was pumped single pass through the lumen of the fiber. Removal of the chromate was typically in the 95% range and the maximum concentration of chromate in the polymer solution was 3% as potassium chromate. The increase in polymer chromate concentration and the amount of residual potassium chromate in the effluent as a function of time is reported in Table XII. The feed stream contained 1000 ppm NaCl to compete with the chromate and the PEI was adjusted to pH 7.0 with HCl to form the cationic extractant. Feed flow rate was 1.00 cc/min. After 50 hours of operation, Example No. 19 was terminated and a separate feed was begun, as Example No. 20, comprising 10,000 ppm potassium chromate and 10,000 ppm sodium chloride. Results are also reported in Table XII.

TABLE XII

Extraction of Chromate with PEI

| Ex. No. | Time (hrs) | Cr (VI) conc[a] in effluent (ppm) | Cr (VI) conc[a] in Polymer (ppm) |
|---|---|---|---|
| 19 | 0   | 400  | 0 |
|    | 5   | 12.5 | 1250 |
|    | 20  | 45   | 9000 |
|    | 30  | 50   | 17500 |
|    | 50  | 190  | 22000 |
| 20 | 100 | 440  | 30000 |

Use of Ground Ion Exchange Resin for Affinity Dialysis

EXAMPLE NO. 21

In order to demonstrate operability of the dialysis process employing ground ion exchange resins as the affinity adsorbent, 5 ml of DOW ion exchange resin XFS 4195.02, a resin selective for copper, was ground to a particle size of 1 to 20 microns, loaded with 0.4 mmoles of zinc ion to pre-equilibrate it, and slurried in 20 ml of water. That slurry was then recirculated at 5 ml/min through the spiral grooves of a modified Amicon CEC-1 unit. A solution of 300 ppm zinc ion and 100 ppm copper ion, both as chlorides, was pumped in a single pass through the porous pad on the underside of the membrane unit. A 5000 molecular weight cutoff membrane composed of an acrylonitrile/polyvinyl alcohol copolymer was used. Feed flow rate was 0.4 ml/min. The reservoir of ion exchange slurry was agitated to maintain a constant suspension.

The outlet aqueous stream (depleted feed) showed a drop in zinc concentration to 70 ppm at 4 hours and then built up to 380 ppm at 22 hours. It remained steady at that level through 40 hours. The copper concentration in the effluent was constant at 10 to 12 ppm after four hours. The rise in zinc beyond the initial feed level was caused by the displacement of zinc by copper which was more tightly bound by the resin. This data is presented in Table XIII which follows.

TABLE XIII

Extraction of Copper from Zinc with Ground Ion Exchange Resin

| Time (hrs) | Effluent | | Resin | |
|---|---|---|---|---|
| | Cu (ppm) | Zn (ppm) | Cu (ppm) | Zn (ppm) |
| 4 | 17.5 | 70 | 320 | 1930 |
| 7 | 15 | 160 | 570 | 2300 |
| 10 | 12.5 | 180 | 840 | 2650 |
| 13 | 12.5 | 160 | 1110 | 3000 |
| 18 | 12.5 | 320 | 1560 | 2900 |
| 22 | 12.5 | 380 | 2010 | 2500 |
| 30 | 16 | 380 | 2730 | 1960 |
| 38 | 30 | 390 | 3270 | 1350 |

Purification and Concentration of a Biological–Nicotinamide Adenine Dinucleotide Reduced Form

EXAMPLE NO. 22

Next, in order to demonstrate the operability of the dialysis process for a biological extraction, nicotinamide adenine dinucleotide reduced (NADH) was extracted with the enzyme alcohol dehydrogenase (ADH) as the affinity adsorbent. An aqueous solution of 100 mM TRIS buffer, a biological buffer, pH 7.5, and 0.25 mM NADH was circulated on one side of an Amicon Cell Culture Hollow Fiber device with 30,000 molecular weight cutoff polysulfone membranes. An aqueous solution 0.5 mM in the enzyme ADH was recirculated on the other side of the membrane. Flow rates were both 2.0 mL per minute. Both solutions were 10 mL in volume. Over a period of 20 hours the transfer of NADH from the feed to the enzyme (adsorbent) solution was monitored. Because the NADH is a known cofactor for ADH enzyme, it was expected that the NADH would migrate to the enzyme side of the membrane and be trapped by the strong binding to the enzyme. In the absence of substrate and at a pH where the enzymatic reaction is disfavored, the NADH should concentrate but not react. The results are presented in following Table XIV.

TABLE XIV

| | Enzyme Extraction | |
|---|---|---|
| Time (hrs) | NADH (mM) | NADH-ADH[a] (mM) |
| 0 | 0.25 | 0.12 |
| 2 | 0.235 | 0.15 |
| 3 | 0.19 | 0.17 |
| 5 | 0.20 | 0.20 |
| 7 | 0.186 | 0.245 |
| 9 | 0.167 | 0.27 |
| 18 | 0.147 | 0.324 |

[a]The reason for the initial NADH in the enzyme solution is that the ADH frequently has some NADH bound to it as recieved.

Stripping of PolyAAMPS

To determine the feasibility of removing bound calcium from the polymer via acidification and dialysis, a polymer solution of 2.5% polyAAMPS loaded with 13,300 ppm calcium as calcium chloride was pumped at 0.25 ml/min countercurrent to a stream of 1.0N HCl (1.06 ml/min). The unit used was the standard hollow fiber unit depicted in FIG. 3 with 150 square cm surface area. Table XV reports the results of the removal. Over 90% of the previously bound Ca was removed with the polymer stream in one pass and an average Ca concentration in the strip stream of about 4000 ppm as calcium chloride was obtained.

TABLE XV

| | Stripping of Calcium from Loaded Polymer | |
|---|---|---|
| Time (hrs) | Ca conc in dialysate[a] (ppm) | Ca conc in product[a] (ppm) |
| 0 | 0 | 4000 |
| 1 | 1800 | 220 |
| 2 | 1600 | 180 |
| 3 | 1500 | 150 |
| 4 | 1500 | 140 |
| 5 | 1400 | 140 |

[a]As Ca

Affinity Dialysis with Stripping and Regeneration Stages

EXAMPLE NO. No. 23

In this next example, two 10,000 sq cm hollow fiber artificial kidneys were used, one to act as the extraction stage and the other to be used as the strip stage. The unit used for the strip side was much larger than required but was used to ensure that the polymer solution was completely stripped prior to regeneration. Concentrated HCl was used to destroy the metal PEI polymer complex and was fed to the reactor as demanded by a pH control unit set at 1.0 pH. After the acid addition step, which occurred in a stirred reactor, the polymer/metal ion solution was stripped with a similar flow rate of pH 2.0 water. The polymer flow rate was 1.0 ml/min and the feed aqueous acid flow was 1.3 ml/min. Feed was 650 ppm Cu and 750 ppm Zn as the chlorides and was pumped through the extraction stage at 30 ml/min. After the strip stage, the polymer solution was regenerated with 50% NaOH using a pH controller set at pH 8.0 whereupon the regenerated polymer solution was returned to the extraction stage. PEI concentration was set at 5%. Data on the operation of the system are presented in Table XVI.

TABLE XVI

| | Combined Extraction Strip and Regeneration Steps | | | |
|---|---|---|---|---|
| | Effluent | | Concentrate | |
| Time (hrs) | Cu (ppm) | Zn (ppm) | Cu (ppm) | Zn[a] (ppm) |
| 0 | 650 | 750 | 0 | 0 |
| 1 | 175 | 650 | 10000 | 3000 |
| 2 | 150 | 700 | 10000 | 1500 |
| 3 | 130 | 650 | 9500 | 3000 |
| 4 | 150 | 700 | 9000 | 1500 |
| 6 | 150 | 720 | 10000 | 900 |
| 7 | 150 | 720 | 10000 | 900 |
| 8 | 140 | 700 | 10000 | 1500 |
| 9 | 150 | 700 | 10000 | 1500 |

[a]Estimate based on feed

Operation of a Scrub Stage

EXAMPLE NO. 24

In this last example, a scrub stage was prepared by loading a 2.5% solution of polyAAMPS with 1,750 ppm Ca ion using the usual affinity dialysis system with a feed of 400 ppm calcium chloride and 1000 ppm sodium chloride. The resulting polymer solution was found to be 1,520 ppm in calcium and 224 ppm in chloride. That solution was pumped through one side of an Amicon CEC-1 membrane unit with a polyacrylonitrile/polyvinylalcohol copolymer membrane with a 5000 molecular weight cutoff. Deionized water was passed on the other side of the membrane at 3.0 ml/min while the polymer solution was fed at 1.0 ml/min. Membrane area was approximately 60 square cm. The objective of this example was to show that removal of the contaminating chloride, presumably there as sodium chloride, would occur without a concomittant loss of calcium. The results were affirmative and are shown in Table XVII.

TABLE XVII

Scrubbing Operation to Remove Chloride Ions from Calcium

| Time (hrs) | Ca (polymer) (ppm) | Ca (wash) (ppm) | Cl (polymer) (ppm) | Cl (wash) (ppm) |
|---|---|---|---|---|
| 0 | 1520 | 0 | 224 | 0 |
| 1 | 1760 | 8.0 | 71 | 51 |
| 2 | 1600 | 4.0 | 73 | 30 |
| 3 | 1680 | 4.8 | 94 | 33 |
| 4 | 1200 | 4.8 | 79 | 28 |
| 6 | 1280 | 5.6 | 87 | 27 |
| 9 | 1600 | 2.4 | 75 | 27 |
| 12 | 1680 | 4.0 | 108 | 29 |

From Table XVII, it is clear that the contaminant is being removed at a greater rate than the calcium by a factor of 125. Hence, a scrub stage can reasonably be expected to improve product purity prior to the stripping of the polymer. In Example No. 24 the contaminant was reduced by about 65% but additional membrane area should reduce that level even further.

Based upon the foregoing disclosure it should be readily apparent that the process of the present invention is useful for the treatment of feed streams containing different materials. The process has been demonstrated to have utility in the selective extraction of metal ions, anions and biological materials, and is capable of both concentrating from dilute solutions as well as exhibiting selectivity to one species over another.

The dialysis process is operable with nearly an infinite number of porous or semipermeable membranes and affinity adsorbent solutions, the latter being selected principally for the chelating or binding properties they have in conjunction with the materials to be extracted from the feed stream. Not only are expensive chelating ion-exchange resins avoided, but the dialysis process eliminates the loss of solvents that may be polluting or expensive or both as characterizes existing solvent extraction and liquid filled membrane systems. It should be understood that variations in the operation such as continuous modes, counter current modes and recycling are included in the present invention as well as the use of mixtures containing several different affinity adsorbents.

In like fashion the dialysis process can be employed with additional steps such as stripping of the loaded adsorbent, scrubbing the loaded adsorbent and regenerating the adsorbent following stripping. The stripping process can also be employed independently of the dialysis process, with or without separate steps of scrubbing and regenerating. Inasmuch as all of these processes can be practiced in a variety of membrane apparatus including artificial kidneys as well as other types of dialysis units, units such as the Amicon cell discussed herein, hollow fiber units, counter-current flow units and the like, it is to be understood that practice of the present invention is not to be limited to any specific form of apparatus.

In conclusion, the examples set forth herein are merely illustrative of operability and are not to be construed as limiting practice of the process to the removal of calcium, copper, chromate and the like or as favoring poly(2-acrylamido-2-methylpropanesulfonic acid), polyethylenimine, ground ion exchange resins or alcohol dehydrogenase as the affinity adsorbents. It is to be understood that any variations evident fall within the scope of the claimed invention; therefore, the selection of specific component members or ingredients can be determined without departing from the spirit of the invention herein disclosed and described. Moreover, the scope of the invention shall include all modifications and variations that may fall within the scope of the attached claims.

I claim:

1. A process for the selective dialysis of liquid streams containing different materials comprising the steps of:
    providing a porous membrane in a cell, said membrane having pores of sufficient dimension to allow passage of said different materials therethrough, wherein said different materials are selected from the group consisting of calcium, sodium, copper, iron, potassium chromate, sodium chloride, reduced nicotinamide adenine dinucleotide and zinc;
    circulating an affinity adsorbent stream miscible with said liquid stream against a first side of said membrane, said affinity adsorbent having a dimension large than that of said pores and having a preferred binding capacity for at least one but not all of said different materials and wherein said affinity adsorbent is selected from the group consisting of alcohol dehydrogenase, polyethylenimine, poly(2-acrylamido-2-methylpropanesulfonic acid) and ground ion exchange resin; and
    passing said liquid stream containing said different materials against a second side of said membrane whereby certain of said materials become bound to said affinity adsorbent upon passing through said membrane to said first side in a concentration greater than their concentration in said liquid stream and thereby become separated from others of said materials which can return to said second side of said membrane.

2. A process as set forth in claim 1, wherein said different materials comprise copper and iron and said affinity adsorbent is polyethylenimine.

3. A process as set forth in claim 1, wherein said different materials comprise copper and iron and said affinity adsorbent is poly(2-acrylamido-2-methylpropanesulfonic acid).

4. A process as set forth in claim 1 , wherein said different materials comprise potassium chromate and sodium chloride and said affinity adsorbent is polyethylenimine.

5. A process as set forth in claim 1, wherein said different material comprises reduced nicotinamide adenine dinucleotide and said affinity adsorbent is alcohol dehydrogenase.

6. A process as set forth in claim 1, wherein said different materials comprise copper and zinc and said affinity adsorbent is ground ion exchange resin.

7. A process as set forth in claim 1, wherein said different materials comprise copper and zinc and said affinity adsorbent is polyethylenimine.

8. A process as set forth in claim 1, comprising the further step of stripping said bound material from said affinity adsorbent, said step of stripping comprising the steps of:

providing a porous membrane in a second cell, said membrane having pores of sufficient dimension to allow passage of said different materials therethrough;

circulating a stripper reagent against a first side of said membrane;

passing said affinity absorbent stream containing at leas tone bound material against a second side of said membrane whereby upon contacting said stripper reagent, said bound different material is released from said affinity absorbent and passes through said membrane to said first side and out of said cell at one end while said stripped affinity absorbent passes out of said cell at a second end.

9. A process a set forth in claim 8, wherein said different materials are selected from the group consisting of calcium, sodium, cooper, iron, potassium chromate, sodium chloride, reduced nicotinamide adenine dinucleotide and zinc; and
  wherein said affinity adsorbent has a molecular weight greater than the size of said pores and is selected from the group consisting of alcohol dehydrogenase, polyethylemimide, poly(2-acrylamido-2-methylpropanesulfonic acid) ground ion exchange resin.

10. A process as set forth in claim 9, wherein said stripper reagent is selected from the group consisting of $Cu^{2+}$ ions, acids capable of lowering the pH of said affinity adsorbent stream to about 4 or lower and bases capable of raising the pH of said affinity adsorbent stream to at least 8 and up to about 10 or higher.

11. A process as set forth in claim 8 comprising the further step of adding a small quantity of said stripper reagent to said affinity adsorbent stream containing at least one bound different material before said stream enters said second cell.

12. A process as set forth in claim 8 wherein said porous membrane is selected from the group consisting of cellulosics, polyphenylene oxides, polysulfones, polyvinylidene halides, polyolefins, polycarbonates, polyimides, polyvinyl alcohol, fluorocarbon polymers, polyacrylonitrile and common substituted analogs thereof and copolymers thereof.

13. A process as set forth in claim 1, comprising the further step of:
  scrubbing said affinity adsorbent stream containing said different materials bound in greater and lesser states of concentration thereto than their respective concentrations in said liquid stream and containing some unbound materials.

14. A process as set forth in claim 13, wherein said step of scrubbing comprises the step of:
  providing a porous membrane in a third cell, said membrane having pores of sufficient dimension to allow passage of said different materials therethrough;
  circulating a solvent for said unbound material against a first side of said membrane;
  passing said affinity adsorbent stream containing at least one bound different material against a second side of said membrane whereby said unbound materials are washed from said affinity adsorbent stream and pass through said membrane to said first side and become separated from said affinity adsorbent and bound materials.

15. A process as set forth in claim 14, comprising the further step of:
  adding a small quantity of said material of greater concentration to said solvent prior to entry into said third cell whereby said material of greater concentration removes a portion of said material of lesser concentration from said affinity adsorbent.

16. A process as set forth in claim 15, wherein said solvent is water.

17. A process as set forth in claim 13 wherein said porous membrane is selected from the group consisting of cellulosics, polyphenylene oxides, polysulfones, polyvinylidene halides, polyolefins, polycarbonates, polyimides, polyvinyl alcohol, fluorocarbon polymers, polyacrylonitrile and common substituted analogs thereof and copolymers thereof.

18. A process as set forth in claim 1, wherein said different materials comprise calcium and sodium and said affinity adsorbent is poly(2-acrylamido-2-methylpropanesulfonic acid).

* * * * *